US008877977B2

(12) United States Patent
Strautmann et al.

(10) Patent No.: US 8,877,977 B2
(45) Date of Patent: Nov. 4, 2014

(54) SYNTHESIS OF POLYALKYLENEPOLYAMINES HAVING A LOW COLOR INDEX BY HOMOGENEOUSLY CATALYZED ALCOHOL AMINATION IN THE PRESENCE OF HYDROGEN

(71) Applicants: Julia Strautmann, Mannheim (DE); Thomas Schaub, Neustadt (DE); Stephan Hueffer, Ludwigshafen (DE); Steffen Maas, Bubenheim (DE); Rocco Paciello, Bad Duerkheim (DE)

(72) Inventors: Julia Strautmann, Mannheim (DE); Thomas Schaub, Neustadt (DE); Stephan Hueffer, Ludwigshafen (DE); Steffen Maas, Bubenheim (DE); Rocco Paciello, Bad Duerkheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/680,625

(22) Filed: Nov. 19, 2012

(65) Prior Publication Data
US 2013/0137901 A1   May 30, 2013

Related U.S. Application Data

(60) Provisional application No. 61/563,657, filed on Nov. 25, 2011.

(51) Int. Cl.
| | |
|---|---|
| C07C 209/16 | (2006.01) |
| C07C 209/60 | (2006.01) |
| C07C 209/68 | (2006.01) |
| C08G 73/02 | (2006.01) |

(52) U.S. Cl.
CPC .......... *C07C 209/68* (2013.01); *C08G 73/0213* (2013.01)
USPC ............................ 564/479; 564/478; 564/480

(58) Field of Classification Search
None
See application file for complete search history.

(56) References Cited

U.S. PATENT DOCUMENTS

| 3,708,539 A | 1/1973 | Fenton et al. |
| 5,977,293 A | 11/1999 | Steuerle et al. |
| 2011/0294977 A1 | 12/2011 | Schaub et al. |

FOREIGN PATENT DOCUMENTS

| DE | 25 30 042 A1 | 1/1977 |
| DE | 195 45 874 A1 | 6/1997 |
| EP | 0 034 480 A2 | 8/1981 |
| EP | 0 239 934 A2 | 10/1987 |
| WO | WO 2011/151268 A1 | 12/2011 |

OTHER PUBLICATIONS

Database CAPLUS on STN, Acc. No. 1959:37512, Newey, US 2,864,775 (Dec. 16, 1958) (abstract).*
Database CAPLUS on STN, Acc. No. 1935:1133, Peacock et al., Journal of the Chemical Society (1934), p. 1303-1305 (abstract).*
Database CAPLUS on STN, Acc. No., 1926:4831, Mann et al., Proceedings of the Royal Society of London, Series A: Mathematical, Physical and Engineering Sciences (1925), 109, p. 444-458 (abstract).*
Database CAPLUS in STN, Acc. No. 1937:41323, Kahane, Bulletin de la Societe Chimique de France, Memoires (1937), 4, p. 717-727 (abstract).*
International Search Report issued Feb. 11, 2013 in PCT/EP2012/073051 with English translation of categories of cited documents.
U.S. Appl. No. 13/948,736, filed Jul. 23, 2013, Schelwies, et al.
Yoshihisa Watanabe, et al., "The Ruthenium Catalyzed N-Alkylation and N-Heterocyclization of Aniline Using Alcohols and Aldehydes", Tetrahedron Letters, vol. 22, No. 28, 1981, pp. 2667-2670.
Ken-ichi Fujita, et al., "Cp*Ir Complex-Catalyzed Hydrogen Transfer Reactions Directed toward Environmentally Benign Organic Synthesis", Synlett, No. 4, 2005, pp. 560-571.
Annegret Tillack, et al., "Salt-Free Synthesis of Tertiary Amines by Ruthenium-Catalyzed Amination of Alcohols", Eur. J. Org. Chem., 2008, pp. 4745-4750.
Annegret Tillack, et al., "A novel ruthenium-catalyzed amination of primary and secondary alcohols", Tetrahedron Letters, 47, 2006, pp. 8881-8885.
Drik Hollmann, et al., "A General Ruthenium-Catalyzed Synthesis of Aromatic Amines", Angew. Chem. Int. Ed., 46, 2007, pp. 8291-8294.
M. Haniti, et al., "Ruthenium-Catalyzed N-Alkylation of Amines and Sulfonamides Using Borrowing Hydrogen Methodology", J. Am. Chem. Soc., 131, 2009, pp. 1766-1774.
Chidambaram Gunanathan, et al., "Selective Synthesis of Primary Amines Directly from Alcohols and Ammonia", Angew. Chem. Int. Ed., 47, 2008, pp. 8661-8664.

* cited by examiner

*Primary Examiner* — Brian J Davis
(74) *Attorney, Agent, or Firm* — Oblon, Spivak, McClelland, Maier & Neustadt, L.L.P.

(57) ABSTRACT

Process for the preparation of polyalkylenepolyamines by homogeneously catalyzed alcohol amination, in which aliphatic amino alcohols are reacted with one another or aliphatic diamines or polyamines are reacted with aliphatic diols or polyols with the elimination of water in the presence of a homogeneous catalyst and in the presence of hydrogen gas. Polyalkylenepolyamines obtainable by such processes and polyalkylenepolyamines comprising hydroxy groups, secondary amines or tertiary amines. Uses of such polyalkylenepolyamines as adhesion promoters for printing inks, adhesion promoters in composite films, cohesion promoters for adhesives, crosslinkers/curing agents for resins, primers for paints, wet-adhesion promoters for emulsion paints, complexing agents and flocculating agents, penetration assistants in wood preservation, corrosion inhibitors, immobilizing agents for proteins and enzymes.

24 Claims, No Drawings

SYNTHESIS OF POLYALKYLENEPOLYAMINES HAVING A LOW COLOR INDEX BY HOMOGENEOUSLY CATALYZED ALCOHOL AMINATION IN THE PRESENCE OF HYDROGEN

The present invention relates to a process for the preparation of polyalkylenepolyamines having a low color index by homogeneously-catalyzed alcohol amination of alkanolamines or of di- or polyamines with diols or polyols in the presence of hydrogen. Furthermore, the invention also relates to polyalkylenepolyamines obtainable by these processes and to the use of polyalkylenepolyamines. The invention further provides specific polyalkylenepolyamines having hydroxy groups, secondary amine groups or tertiary amine groups.

Further embodiments of the present invention can be found in the claims, the description and the examples. It goes without saying that the features of the subject matter according to the invention that have been specified above and are still to be explained below can be used not only in the combination specifically stated in each case, but also in other combinations, without departing from the scope of the invention. The embodiments of the present invention in which all features have the preferred or very preferred meanings are preferred or very preferred, respectively.

Polyethyleneimines are valuable products with a large number of different uses. For example, polyethyleneimines are used: a) as adhesion promoters for printing inks for laminate films; b) as auxiliaries (adhesion) for producing multiply composite films, where not only are different polymer layers compatibilized, but also metal films; c) as adhesion promoters for adhesives, for example in conjunction with polyvinyl alcohol, butyrate and acetate and styrene copolymers, or as cohesion promoter for label adhesives; d) low molecular weight polyethyleneimines can moreover be used as crosslinkers/hardeners in epoxy resins and polyurethane adhesives; e) as primers in coating applications for improving adhesion on substrates such as glass, wood, plastic and metal; f) for improving wet adhesion in standard emulsion paints and also for improving the instantaneous rain resistance of paints for example for road markings; g) as complexing agent with high binding capacity for heavy metals such as Hg, Pb, Cu, Ni and flocculants in water treatment/water processing; h) as penetration auxiliaries for active metal salt formulations in wood preservation; i) as corrosion inhibitors for iron and nonferrous metals; j) for the immobilization of proteins and enzymes. For these applications, it is also possible to use polyalkylenepolyamines which are not derived from the ethyleneimine.

Polyethyleneimines are currently obtained by the homopolymerization of ethyleneimine. Ethyleneimine is a highly reactive, corrosive and toxic intermediate which can be synthesized in different ways (aziridines, Ulrich Steuerle, Robert Feuerhake; in Ullmann's Encyclopedia of Industrial Chemistry, 2006, Wiley-VCH, Weinheim).

In the β-chloroethylamine process, ethyleneimine is obtained by reacting β-chloroethylamine with NaOH. This process may lead to the undesired polymerization of the β-chloroethylamine by HCl elimination, which must be carefully avoided. Moreover, the use of two equivalents of NaOH and the formation of the coproduct NaCl is disadvantageous.

In the Dow process, the ethyleneimine can be obtained by reacting 1,2-dichloroethane with three equivalents of ammonia. The use of large amounts of ammonia, the formation of the coproduct ammonium chloride, the corrosivity of the reaction mixture and also impurities in the product are disadvantageous.

In the Wencker process, in the first step, 2-aminoethanol is reacted with sulfuric acid to give 2-aminoethyl hydrogensulfate. The ethyleneamine is then obtained from this in the second step by adding two equivalents of NaOH. Here too, the use of sulfuric acid and NaOH and also the formation of the coproduct sodium sulfate are disadvantageous.

During the catalytic dehydrogenation of 2-aminoethanol, the ethyleneimine is obtained by the catalytic dehydrogenation of 2-aminoethanol in the gas phase at 250-450° C. Disadvantages of this process are the complex product work-up by distillation, the high energy requirement and also the short catalyst life.

Besides the stated disadvantages of the processes for the preparation of ethyleneimine, the synthesis of polyethyleneimines starting from this starting compound is problematic since the highly reactive, toxic and corrosive ethyleneimine has to be handled. It likewise has to be ensured that no ethyleneimine remains in the products obtained and/or wastewater streams.

For the preparation of polyalkylenepolyamines —[(CH$_2$)$_x$N]— with alkylene groups >C$_2$(x>2) not derived from aziridine, there are no processes analogous to the aziridine route, as a result of which there has hitherto been no cost-effective process for their preparation.

The homogenously catalyzed amination of alcohols is known from the literature for the synthesis of primary, secondary and tertiary amines starting from alcohols and amines, with monomeric products being obtained in all of the described embodiments.

U.S. Pat. No. 3,708,539 describes the synthesis of primary, secondary and tertiary amines using a ruthenium-phosphane complex.

Y. Watanabe, Y. Tsuji, Y. Ohsugi Tetrahedron Lett. 1981, 22, 2667-2670 reports on the preparation of arylamines by the amination of alcohols with aniline using [Ru(PPh$_3$)$_3$Cl$_2$] as catalyst.

EP 0 034 480 A2 discloses the preparation of N-alkyl- or N,N-dialkylamines by the reaction of primary or secondary amines with a primary or secondary alcohol using an iridium, rhodium, ruthenium, osmium, platinum, palladium or rhenium catalyst.

EP 0 239 934 A1 describes the synthesis of mono- and diaminated products starting from diols such as ethylene glycol and 1,3-propanediol with secondary amines using ruthenium and iridium phosphane complexes.

K. I. Fujita, R. Yamaguchi Synlett, 2005, 4, 560-571 describes the synthesis of secondary amines by the reaction of alcohols with primary amines and also the synthesis of cyclic amines by the reaction of primary amines with diols by ring closure using iridium catalysts.

In A. Tillack, D. Hollmann, K. Mevius, D. Michalik, S. Ban, M. Beller Eur. J. Org. Chem. 2008, 4745-4750, in A. Tillack, D. Hollmann, D. Michalik, M. Beller Tetrahedron Lett. 2006, 47, 8881-8885, in D. Hollmann, S. Bahn, A. Tillack, M. Beller Angew. Chem. Int. Ed. 2007, 46, 8291-8294 and in M. Haniti, S. A. Hamid, C. L. Allen, G. W. Lamb, A. C. Maxwell, H. C. Maytum, A. J. A. Watson, J. M. J. Williams J. Am. Chem. Soc, 2009, 131, 1766-1774 syntheses of secondary and tertiary amines starting from alcohols and primary or secondary amines using homogeneous ruthenium catalysts are described.

The synthesis of primary amines by reacting alcohols with ammonia using a homogeneous ruthenium catalyst is reported in C. Gunanathan, D. Milstein Angew. Chem. Int. Ed. 2008, 47, 8661-8664.

Our unpublished application PCT/EP2011/058758 describes general processes for the preparation of polyalkylenepolyamines by catalytic alcohol amination of alkanolamines or of diamines or polyamines with diols or polyols.

It is an object of the present invention to find a process for the preparation of polyalkylenepolyamines in which no aziridine is used, no undesired coproducts are formed, products of a desired chain length are obtained and the color index of the product is as low as possible.

The object is achieved by a process for the preparation of polyalkylenepolyamines by homogeneously catalyzed alcohol amination, in which (i) aliphatic amino alcohols with one another or (ii) aliphatic diamines or polyamines with aliphatic diols or polyols with the elimination of water in the presence of a homogeneous catalyst and hydrogen gas. This reaction preferably takes place under pressures of between 0.1 and 25 MPa and at temperatures of between 100 and 200° C.

Within the context of this invention, expressions of the form $C_a$-$C_b$ refer to chemical compounds or substituents with a certain number of carbon atoms. The number of carbon atoms can be selected from the entire range from a to b, including a and b, a is at least 1 and b is always greater than a. The chemical compounds or substituents are further specified by expressions of the form $C_a$-$C_b$-V. V here stands for a chemical compound class or substituent class, for example alkyl compounds or alkyl substituents.

Specifically, the collective terms stated for the various substituents have the following meaning:

$C_1$-$C_{50}$-Alkyl: straight-chain or branched hydrocarbon radicals having up to 50 carbon atoms, for example $C_1$-$C_{10}$-alkyl or $C_{11}$-$C_{20}$-alkyl, preferably $C_1$-$C_{10}$-alkyl, for example $C_1$-$C_3$-alkyl, such as methyl, ethyl, propyl, isopropyl, or C4-C6-alkyl, n-butyl, sec-butyl, tert-butyl, 1,1-dimethylethyl, pentyl, 2-methylbutyl, 1,1-dimethylpropyl, 1,2-dimethylpropyl, 2,2-dimethylpropyl, 1-ethylpropyl, hexyl, 2-methylpentyl, 3-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 2-ethylbutyl, 1,1,2-trimethylpropyl, 1,2,2-trimethylpropyl, 1-ethyl-1-methylpropyl, 1-ethyl-2-methylpropyl, or $C_7$-$C_{10}$-alkyl, such as heptyl, octyl, 2-ethylhexyl, 2,4,4-trimethylpentyl, 1,1,3,3-tetramethylbutyl, nonyl or decyl, and isomers thereof.

$C_3$-$C_{15}$-Cycloalkyl: monocyclic, saturated hydrocarbon groups having from 3 up to 15 carbon ring members, preferably $C_3$-$C_8$-cycloalkyl such as cyclopropyl, cyclobutyl, cyclopentyl, cyclohexyl, cycloheptyl or cyclooctyl, and also a saturated or unsaturated cyclic system such as e.g. norbornyl or norbenyl.

Aryl: a mono- to trinuclear aromatic ring system comprising 6 to 14 carbon ring members, e.g. phenyl, naphthyl or anthracenyl, preferably a mono- to dinuclear, particularly preferably a mononuclear, aromatic ring system.

Within the context of the present invention, the symbol "*" indicates, for all chemical compounds, the valence via which one chemical group is bonded to another chemical group.

Polyalkylenepolyamines can be obtained by reacting (i) aliphatic amino alcohols with one another, or (ii) aliphatic diamines or polyamines with aliphatic diols or polyols, in each case in the presence of a catalyst. Surprisingly it has been found that the color number of the product decreases if hydrogen is injected during the reaction. The comparison used for this in each case is the product synthesized in the same way but without hydrogen. In accordance with the invention, therefore, polyalkylenepolyamines of lower color number are obtained if hydrogen is injected before or during the synthesis of the polyalkylenepolyamines, i.e., the reaction takes place in the presence of hydrogen gas. The injection of hydrogen gas is carried out preferably with pressures of 0.1 to 25 MPa (partial pressure of hydrogen gas), more preferably of 1 to 10 MPa and more particularly of 1 to 7 MPa. A temperature is set preferably of between 100 and 200° C., more preferably 130 to 180° C. As a result of the injection of the hydrogen, the color number is reduced by a factor of at least 2, preferably by a factor of 10 to 100.

Aliphatic amino alcohols which are suitable for a reaction under hydrogen atmosphere comprise at least one primary or secondary amino group and at least one OH group. Examples are linear, branched or cyclic alkanolamines such as monoethanolamine, diethanolamine, aminopropanol, for example 3-aminopropan-1-ol or 2-aminopropan-1-ol, aminobutanol, for example 4-aminobutan-1-ol, 2-aminobutan-1-ol or 3-aminobutan-1-ol, aminopentanol, for example 5-aminopentan-1-ol or 1-aminopentan-2-ol, aminodimethylpentanol, for example 5-amino-2,2-dimethylpentanol, aminohexanol, for example 2-aminohexan-1-ol or 6-aminohexan-1-ol, aminoheptanol, for example 2-aminoheptan-1-ol or 7-aminoheptan-1-ol, aminooctanol, for example 2-aminooctan-1-ol or 8-aminooctan-1-ol, aminononanol, for example 2-aminononan-1-ol or 9-aminononan-1-ol, aminodecanol, for example 2-aminodecan-1-ol or 10-aminodecan-1-ol, aminoundecanol, for example 2-aminoundecan-1-ol or 11-aminoundecan-1-ol, aminododecanol, for example 2-aminododecan-1-ol or 12-aminododecan-1-ol, aminotridecanol, for example 2-aminotridecan-1-ol, 1-(2-hydroxyethyl)piperazine, 2-(2-aminoethoxy)ethanol, alkylalkanolamines, for example butylethanolamine, propylethanolamine, ethylethanolamine, methylethanolamine. Particular preference is given to monoethanolamine and monopropanolamine.

Aliphatic diamines which are suitable for a reaction under hydrogen atmosphere comprise at least two primary or at least one primary and one secondary or at least two secondary amino groups, they preferably comprise two primary amino groups. Examples are linear, branched or cyclic aliphatic diamines. Examples are ethylenediamine, 1,3-propylenediamine, 1,2-propylenediamine, butylenediamine, for example 1,4-butylenediamine or 1,2-butylenediamine, diaminopentane, for example 1,5-diaminopentane or 1,2-diaminopentane, 1,5-diamino-2-methylpentane, diaminohexane, for example 1,6-diaminohexane or 1,2-diaminohexane, diaminoheptane, for example 1,7-diaminoheptane or 1,2-diaminoheptane, diaminooctane, for example 1,8-diaminooctane or 1,2-diaminooctane, diaminononane, for example 1,9-diaminononane or 1,2-diaminononane, diaminodecane, for example 1,10-diamino-decane or 1,2-diaminodecane, diaminoundecane, for example 1,11-diaminoundecane or 1,2-diaminoundecane, diaminododecane, for example 1,12-diaminododecane or 1,2-diamino-dodecane, 3,3'-dimethyl-4,4'-diaminodicyclohexylmethane, 4,4'-diaminodicyclohexylmethane, isophoronediamine, 2,2-dimethylpropane-1,3-diamine, 4,7,10-trioxatridecane-1,13-diamine, 4,9-dioxadodecane-1,12-diamine, polyetheramines, piperazine, 3-(cyclohexylamino)propylamine, 3-(methylamino)propylamine, N,N-bis(3-aminopropyl)methylamine.

Suitable aliphatic diols are linear, branched or cyclic aliphatic diols. Examples of aliphatic diols are ethylene glycol, 1,2-propylene glycol, 1,3-propylene glycol, 2-methyl-1,3-propanediol, butanediols, for example 1,4-butylene glycol or butane-2,3-diol or 1,2-butylene glycol, pentanediols, for example neopentyl glycol or 1,5-pentanediol or 1,2-pentanediol, hexanediols, for example 1,6-hexanediol or 1,2-hexanediol, heptanediols, for example 1,7-heptanediol or 1,2-heptanediol, octanediols, for example 1,8-octanediol or 1,2-octanediol, nonanediols, for example 1,9-nonanediol or 1,2-nonanediol, decanediols, for example 1,10-decanediol or 1,2-decanediol, undecanediols, for example 1,11-undecanediol or 1,2-undecanediol, dodecanediols, for example 1,12-dodecanediol, 1,2-dodecanediol, tridecanediols, for example 1,13-tridecanediol or 1,2-tridecanediol, tetradecanediols, for example 1,14-tetradecanediol or 1,2-tetradecanediol, pentadecanediols, for example 1,15-pentadecanediol or 1,2-pentadecanediol, hexadecanediols, for example 1,16-hexadecanediol or 1,2-hexadecanediol, heptadecanediols, for example 1,17-heptadecanediol or 1,2-heptadecanediol, octadecanediols, for example 1,18-octadecanediol or 1,2-octadecanediol, 3,4-dimethyl-2,5-hexanediol, polyTHF, 1,4-bis(2-hydroxyethyl)piperazine, diethanolamines, for example butyldiethanolamine or methyldiethanolamine, dialcoholamines and trialcoholamines.

Preferred polyalkylenepolyamines obtainable according to the invention under hydrogen atmosphere comprise $C_2$-$C_{50}$-alkylene units, particularly preferably $C_2$-$C_{20}$-alkylene units. These can be linear or branched, they are preferably linear. Examples are ethylene, propylene, for example 1,3-propylene, butylene, for example 1,4-butylene, pentylene, for example 1,5-pentylene or 1,2-pentylene, hexylene, for example 1,6-hexylene, octylene, for example 1,8-octylene or 1,2-octylene, nonylene, for example 1,9-nonylene or 1,2-nonylene, decylene, for example 1,2-decylene or 1,10-decylene, undecylene, for example 1,2-undecylene, dodecylene, for example 1,12-dodecylene or 1,2-dodecylene, tridecylene, for example 1,2-tridecylene, octyl, nonyl, decyl, undecyl, dodecyl, tridecyl, neopentylene. Cycloalkylene units are also possible, for example 1,3- or 1,4-cyclohexylene. The polyalkylenepolyamines particularly preferably have $C_2$-alkylene units.

It is also possible to use mixtures of aliphatic amino alcohols or mixtures of alkanediols or mixtures of diaminoalkanes in the respective reactions under hydrogen pressure. The resulting polyalkylenepolyamines can comprise alkylene units of different length.

Polyfunctional amino alcohols having more than one OH group or more than one primary or secondary amino group can also be reacted with one another under hydrogen pressure. In this case, highly branched products are obtained. Examples of polyfunctional amino alcohols are diethanolamine, N-(2-aminoethyl)ethanolamine, diisopropanolamine, diisononanolamine, diisodecanolamine, diisoundecanolamine, diisododecanolamine, diisotridecanolamine.

Polyols or mixtures of diols and polyols can also be reacted with diamines under hydrogen pressure. Polyamines or mixtures of diamines and polyamines can also be reacted with diols. Polyols or mixtures of diols and polyols can also be reacted with polyamines or mixtures of diamines and polyamines. In this case, highly branched products are obtained. Examples of polyols are glycerol, trimethylolpropane, sorbitol, triethanolamine, triisopropanolamine. Examples of polyamines are diethylenetriamine, tris(aminoethyl)amine, triazine, 3-(2-aminoethylamino)propylamine, dipropylenetriamine, N,N'-bis(3-aminopropyl)ethylenediamine.

Particularly suitable compounds are those in which at least one of the starting materials aliphatic amino alcohols, aliphatic diamines or polyamines or aliphatic diols or polyols comprises an alkyl or alkylene group having from 2 to 4 carbon atoms.

Compounds particularly suitable for the reaction under hydrogen pressure are likewise those in which at least one of the starting materials aliphatic amino alcohols, aliphatic diamines or polyamines or aliphatic diols or polyols comprises an alkyl or alkylene group having five or more, preferably seven or more, particularly preferably nine or more, in particular twelve or more, carbon atoms.

Particularly suitable compounds are those in which at least one of the starting materials aliphatic amino alcohols, aliphatic diamines or polyamines or aliphatic diols or polyols comprises an alkyl or alkylene group having from 5 to 50, preferably from 5 to 20, particularly preferably from 6 to 18, very particularly preferably from 7 to 16, especially preferably from 8 to 14 and in particular from 9 to 12 carbon atoms.

For the synthesis, preference is given to selecting at least (i) monoethanolamine, (ii) monopropanolamine or (iii) ethylene glycol with ethylenediamine. Furthermore, preferably at least (i) ethylenediamine or (ii) 1,2-propylenediamine or (iii) 1,3-propylenediamine and 1,2-decanediol or 1,2-dodecanediol are preferably selected.

Hydroxy and amino groups in diols, polyols and diamines, polyamines are preferably used in molar ratios of from 20:1 to 1:20, particularly preferably in ratios of from 8:1 to 1:8, in particular from 3:1 to 1:3.

Polyalkylenepolyamines can also be reacted under hydrogen pressure. During the reaction, diamines or polyamines or diols or polyols or amino alcohols can be added.

Hydrogen can be injected while the water of reaction is removed from the system continuously or discontinuously.

The preparation of the polyalkylenepolyamines is illustrated by way of example in equation 2 and 2:

Equation 1

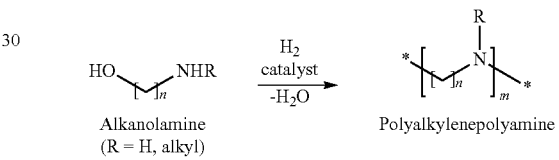

Alkanolamine (R = H, alkyl)   Polyalkylenepolyamine

Equation 2

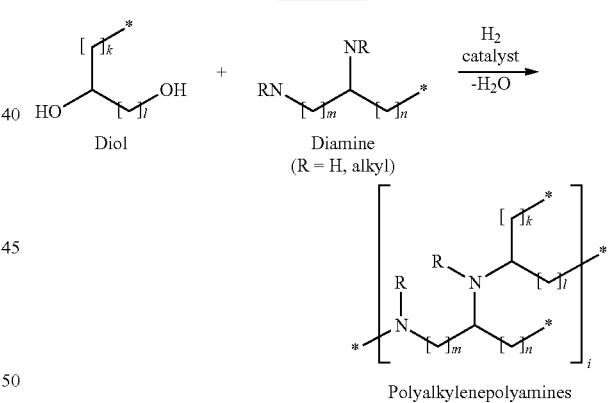

Diol   Diamine (R = H, alkyl)

Polyalkylenepolyamines

A homogeneous catalyst is understood as meaning a catalyst which is present in the reaction medium in homogeneously dissolved form during the reaction.

The homogeneous catalyst generally comprises at least one element of the sub-groups of the Periodic Table of the Elements (transition metal). The alcohol amination under hydrogen pressure can be carried out in the presence or absence of an additional solvent. The alcohol amination can be carried out in a multiphase, preferably one-phase or two-phase, liquid system at temperatures of generally 20 to 250° C. In the case of two-phase reaction systems, the upper phase can consist of a nonpolar solvent, which comprises the majority of the homogeneously dissolved catalyst, and the lower phase comprising the polar starting materials, the polyamines formed and also water. Furthermore, the lower phase can consist of water and also the homogeneously dissolved catalyst and the upper phase can consist of a nonpolar solvent which comprises the majority of the polyamines formed and the nonpolar starting materials.

In a preferred embodiment of the invention, (i) monoethanolamine or (ii) monopropanolamine or (iii) diamines selected from ethylenediamine, 1,3-propylenediamine or 1,2-propylenediamine is reacted with diols selected from ethylene glycol, 1,2-decanediol or 1,2-dodecanediol in the presence of a homogeneous catalyst and under a hydrogen pressure of from 1 to 10 MPa and with removal of the water that is formed during the reaction.

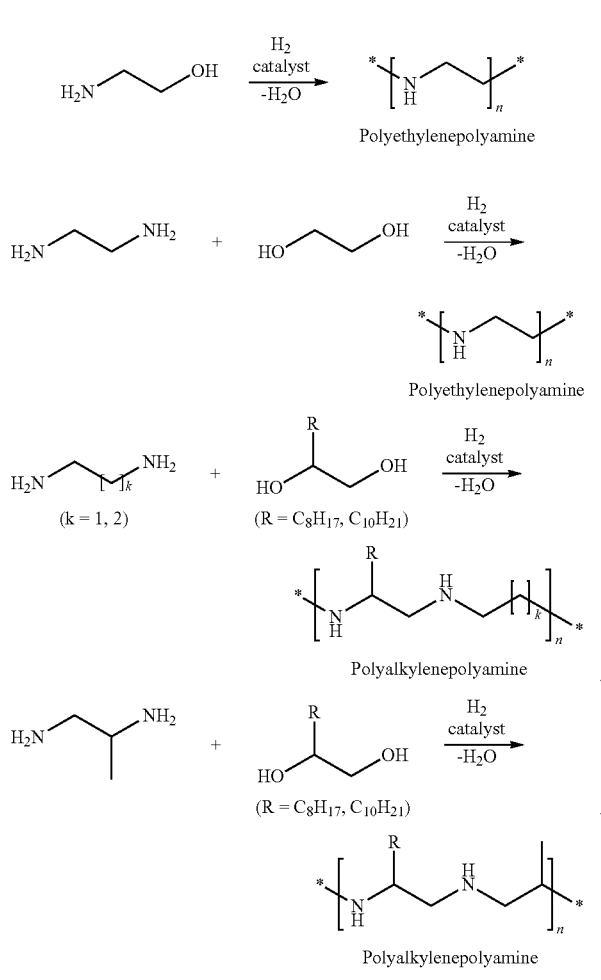

The number of alkylene units n in the polyalkylenepolyamines is generally between 3 and 50 000.

The polyalkylenepolyamines thus obtained can carry both $NH_2$ and also OH groups as end groups at the chain ends.

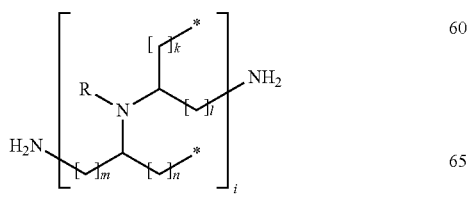

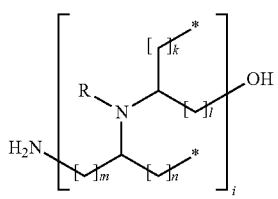

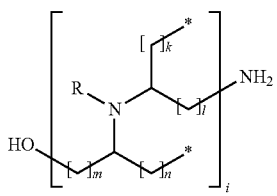

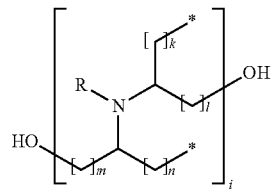

where preferably

R independently of one another, are identical or different and are H, $C_1$-$C_{50}$-alkyl, l, m independently of one another, are identical or different and are an integer from the range from 1 to 50, preferably from 1 to 30, particularly preferably from 1 to 20, n, k independently of one another, are identical or different and are an integer from the range from 0 to 50, preferably from 0 to 30, particularly preferably from 0 to 20, i is an integer from the range from 3 to 50 000.

The number-average molecular weight Mn of the polyalkylenepolyamines obtained is generally from 200 to 2 000 000, preferably from 400 to 750 000 and particularly preferably from 400 to 50 000. The molar mass distribution Mw/Mn is generally in the range from 1.2 to 20, preferably from 1.5-7.5. The cationic charge density (at pH 4-5) is generally in the range from 4 to 22 mequ/g of dry substance, preferably in the range from 6 to 18 mequ/g.

The polyalkylenepolyamines obtained by the process according to the invention can be present either in linear form or in branched or multi-branched form, and also have ring-shaped structural units.

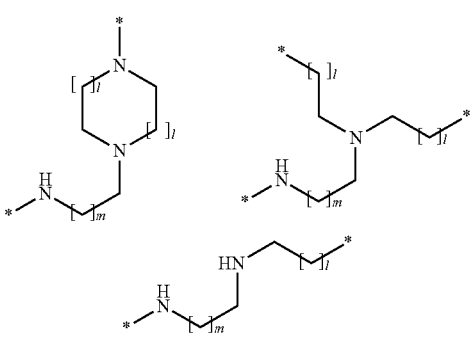

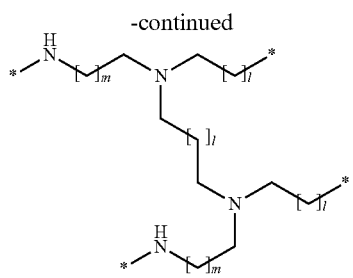

In this connection, the distribution of the structural units (linear, branched or cyclic) is random. The polyalkylenepolyamines thus obtained differ from the polyethyleneimines prepared from ethyleneimine by virtue of the OH end groups present and also optionally by virtue of different alkylene groups.

The homogeneous catalyst is preferably a transition metal complex catalyst which comprises one or more different metals of the sub-groups of the Periodic Table of the Elements, preferably at least one element from groups 8, 9 and 10 of the Periodic Table of the Elements, particularly preferably ruthenium or iridium. The specified sub-group metals are present in the form of complex compounds. Numerous different ligands are contemplated.

Suitable ligands present in the transition metal complex compounds are, for example, phosphines substituted with alkyl or aryl, polydentate phosphines substituted with alkyl or aryl which are bridged via arylene or alkylene groups, nitrogen-heterocyclic carbenes, cyclopentanedienyl and pentamethylcyclopentadienyl, aryl, olefin ligands, hydride, halide, carboxylate, alkoxylate, carbonyl, hydroxide, trialkylamine, dialkylamine, monoalkylamine, nitrogen aromatics such as pyridine or pyrrolidine and polydentate amines. The organometallic complex can comprise one or more different specified ligands.

Preferred ligands are (monodentate) phosphines or (polydentate) polyphosphines, for example diphosphines, with at least one unbranched or branched, acyclic or cyclic, aliphatic, aromatic or araliphatic radical having 1 to 20, preferably 1 to 12 carbon atoms. Examples of branched cycloaliphatic and araliphatic radicals are —$CH_2$—$C_6H_{11}$ and —$CH_2$—$C_6H_5$. Suitable radicals which may be mentioned by way of example are: methyl, ethyl, 1-propyl, 2-propyl, 1-butyl, 2-butyl, 1-(2-methyl)propyl, 2-(2-methyl)propyl, 1-pentyl, 1-hexyl, 1-heptyl, 1-octyl, 1-nonyl, 1-decyl, 1-undecyl, 1-dodecyl, cyclopentenyl, cyclohexyl, cycloheptyl and cyclooctyl, methylcyclopentyl, methylcyclohexyl, 1-(2-methyl)pentyl, 1-(2-ethyl)hexyl, 1-(2-propylheptyl), adamantyl and norbornyl, phenyl, tolyl and xylyl, and 1-phenylpyrrole, 1-(2-methoxyphenyl)pyrrole, 1-(2,4,6-trimethylphenyl)imidazole and 1-phenylindole. The phosphine group can comprise two or three of the specified unbranched or branched, acyclic or cyclic, aliphatic, aromatic or araliphatic radicals. These may be identical or different.

Preferably, the homogeneous catalyst comprises a monodentate or polydentate phosphine ligand comprising an unbranched, acyclic or cyclic aliphatic radical having from 1 to 12 carbon atoms or an aryliphatic radical or adamantyl or 1-phenylpyrrole as radical.

In the specified unbranched or branched, acyclic or cyclic, aliphatic, aromatic or araliphatic radicals, individual carbon atoms can also be substituted by further phosphine groups. Also comprised are thus polydentate, for example bi- or tridentate, phosphine ligands, the phosphine groups of which are bridged by alkylene or arylene groups. The phosphine groups are preferably bridged by 1,2-phenylene, methylene, 1,2-ethylene, 1,2-dimethyl-1,2-ethylene, 1,3-propylene, 1,4-butylene and 1,5-propylene bridges.

Particularly suitable monodentate phosphine ligands are triphenylphosphine, tritolylphosphine, tri-n-butylphosphine, tri-n-octylphosphine, trimethylphosphine and triethylphosphine, and also di(1-adamantyl)-n-butylphosphine, di(1-adamantyl)benzylphosphine, 2-(dicyclohexylphosphino)-1-phenyl-1H-pyrrole, 2-(dicyclohexylphosphino)-1-(2,4,6-trimethylphenyl)-1H-imidazole, 2-(dicyclohexylphosphino)-1-phenylindole, 2-(di-tert-butylphosphino)-1-phenylindole, 2-(dicyclohexylphosphino)-1-(2-methoxyphenyl)-1H-pyrrole, 2-(di-tert-butylphosphino)-1-(2-methoxyphenyl)-1H-pyrrole and 2-(di-tert-butylphosphino)-1-phenyl-1H-pyrrole. Very particular preference is given to triphenylphosphine, tritolylphosphine, tri-n-butylphosphine, tri-n-octyl-phosphine, trimethylphosphine and triethylphosphine, and also di(1-adamantyl)-n-butyl-phosphine, 2-(dicyclohexylphosphino)-1-phenyl-1H-pyrrole and 2-(di-tert-butylphosphino)-1-phenyl-1H-pyrrole.

Particularly suitable polydentate phosphine ligands are bis(diphenylphosphino)methane, 1,2-bis(diphenylphosphino)ethane, 1,2-dimethyl-1,2-bis(diphenylphosphino)ethane, 1,2-bis(dicyclohexylphosphino)ethane, 1,2-bis(diethylphosphino)ethane, 1,3-bis(diphenyl-phosphino)propane, 1,4-bis(diphenylphosphino)butane, 2,3-bis(diphenylphosphino)butane, 1,3-bis(diphenylphosphino)propane, 1,1,1-tris(diphenylphosphinomethyl)ethane, 1,1'-bis(diphenylphosphanyl)ferrocene and 4,5-bis(diphenylphosphino)-9,9-dimethylxanthene.

Furthermore, mention may preferably be made of nitrogen-heterocyclic carbenes as particularly suitable ligands. In this connection, those ligands which form water-soluble complexes with Ru are very preferred. Particular preference is given to 1-butyl-3-methylimidazolin-2-ylidene, 1-ethyl-3-methylimidazolin-2-ylidene, 1-methylimidazolin-2-ylidene and dipropylimidazolin-2-ylidene.

Particularly suitable ligands which may be mentioned are also cyclopentadienyl and its derivatives mono- to pentasubstituted with alkyl, aryl and/or hydroxy, such as, for example, methylcyclopentadienyl, pentamethylcyclopentadienyl, tetraphenylhydroxycyclopentadienyl and pentaphenylcyclopentadienyl. Further particularly suitable ligands are indenyl and its derivatives substituted as described for cyclopentadienyl.

Likewise particularly suitable ligands are chloride, hydride and carbonyl.

The transition metal complex catalyst can of course comprise two or more different or identical ligands described above.

The homogeneous catalysts can be used either directly in their active form or else be produced starting from customary standard complexes such as, for example, [Ru(p-cymene)$Cl_2]_2$, [Ru(benzene)$Cl_2]_n$, [Ru(CO)$_2Cl_2]_n$, [Ru(CO)$_3Cl_2]_2$, [Ru(COD)(allyl)], [RuCl$_3$*H$_2$O], [Ru(acetylacetonate)$_3$], [Ru(DMSO)$_4Cl_2$], [Ru(PPh$_3$)$_3$(CO)(H)Cl], [Ru(PPh$_3$)$_3$(CO)Cl$_2$], [Ru(PPh$_3$)$_3$(CO)(H)$_2$], [Ru(PPh$_3$)$_3Cl_2$], [Ru(cyclopentadienyl)(PPh$_3$)$_2$Cl], [Ru(cyclopentadienyl)(CO)$_2$Cl], [Ru(cyclopentadienyl)(CO)$_2$H], [Ru(cyclopentadienyl)(CO)$_2$]$_2$, [Ru(pentamethylcyclopentadienyl)(CO)$_2$Cl], [Ru(pentamethylcyclopentadienyl)(CO)$_2$H], [Ru(pentamethylcyclopentadienyl)(CO)$_2$]$_2$, [Ru(indenyl)(CO)$_2$Cl], [Ru(indenyl)(CO)$_2$H], [Ru(indenyl)(CO)$_2$]$_2$, ruthenocene, [Ru(binap)Cl$_2$], [Ru(bipyridine)$_2$Cl$_2$*2H$_2$O], [Ru(COD)Cl$_2$]$_2$, [Ru(pentamethylcyclopentadienyl)(COD)Cl], [Ru$_3$(CO)$_{12}$], [Ru(tetraphenylhydroxy-cyclopentadienyl)(CO)$_2$H], [Ru(PMe$_3$)$_4$(H)$_2$], [Ru(PEt$_3$)$_4$(H)$_2$], [Ru(PnPr$_3$)$_4$(H)$_2$], [Ru(PnBu$_3$)$_4$ (H)$_2$], [Ru(PnOctyl$_3$)$_4$(H)$_2$], [IrCl$_3$*H$_2$O], KIrCl$_4$, K$_3$IrCl$_6$, [Ir(COD)Cl]$_2$, [Ir(cyclooctene)$_2$Cl]$_2$, [Ir(ethene)$_2$Cl]$_2$, [Ir(cyclopentadienyl)Cl$_2$]$_2$, [Ir(pentamethylcyclopentadienyl)Cl$_2$]$_2$, [Ir(cyclopenta-dienyl)(CO)$_2$], [Ir(pentamethylcyclopentadienyl)(CO)$_2$], [Ir(PPh$_3$)$_2$(CO)(H)], [Ir(PPh$_3$)$_2$(CO)(Cl)], [Ir(PPh$_3$)$_3$(Cl)] with the addition of the corresponding ligands, preferably the aforementioned mono- or polydentate phosphine ligands or the aforementioned nitrogen-heterocyclic carbenes, only under the reaction conditions.

The amount of the metal component in the catalyst, preferably ruthenium or iridium, is generally 0.1 to 5000 ppm by weight, in each case based on the total liquid reaction mixture.

The process according to the invention can be carried out either in a solvent or without solvent. The process according to the invention can of course also be carried out in a solvent mixture.

If the process is carried out in a solvent, then the amount of solvent is often selected such that the starting materials (i) and (ii) just dissolve in the solvent. In general, the weight ratio of the amount of solvent to the amount of starting materials (i) and (ii) is from 100:1 to 0.1:1, preferably from 10:1 to 0.1:1.

The reaction according to the invention takes place in the liquid phase at a temperature of generally 20 to 250° C. Preferably, the temperature is at least 100° C. and preferably at most 200° C. The reaction can be carried out at a total pressure of from 0.1 to 25 MPa absolute, which may be either the pressure of hydrogen in combination with the intrinsic pressure of the solvent at the reaction temperature or else the pressure of a gas such as nitrogen or argon in combination with hydrogen. The average reaction time is generally 15 minutes to 100 hours.

The addition of bases can have a positive effect on the product formation. Suitable bases which may be mentioned here are alkali metal hydroxides, alkaline earth metal hydroxides, alkali metal alcoholates, alkaline earth metal alcoholates, alkali metal carbonates and alkaline earth metal carbonates, of which 0.01 to 100 equivalents can be used based on the metal catalyst used.

In a preferred embodiment of the process according to the invention, the heteroatoms O or N of one of the starting materials (i) aliphatic amino alcohols, (ii) aliphatic diamines or polyamines or aliphatic diols or polyols are located in alpha and beta position on the chain of carbon atoms and thus on adjacent carbon atoms.

In a preferred embodiment of the process according to the invention, the heteroatoms O or N of one of the starting materials (i) aliphatic amino alcohols, (ii) aliphatic diamines or polyamines or aliphatic diols or polyols are located in alpha and omega position on the chain of carbon atoms and thus at opposite ends of the chain of carbon atoms.

The invention further provides polyalkylenepolyamines, preferably polyethylenamine or polypropylenamine, which are prepared by the described embodiments of the process according to the invention.

A further subject of the invention are polyalkylenepolyamines which comprise hydroxy groups, secondary amines or tertiary amines. The hydroxy groups, secondary amines or tertiary amines are preferably located on a terminal carbon atom of an alkylene group, and therefore constitute an end group. These polyalkylenepolyamines preferably comprise hydroxy groups.

These polyalkylenepolyamines which comprise hydroxy groups, secondary amines or tertiary amines are obtainable for example with the aid of the process according to the invention. More particularly these polyalkylenepolyamines are obtained in a process by the polymerization of monomers in one step.

Preferably the ratio of the number of hydroxy end groups to amine end groups (primary, secondary, tertiary) is from 10:1 to 1:10, preferably from 5:1 to 1:5, more preferably from 2:1 to 1:2.

In another preferred embodiment those polyalkylenepolyamines which comprise hydroxy groups, secondary amines or tertiary amines have only hydroxy end groups or only amine end groups (primary, secondary, tertiary).

The invention also relates to the uses of the polyalkylenepolyamines a) as adhesion promoters for printing inks, b) as auxiliaries (adhesion) for the production of composite films, c) as cohesion promoters for adhesives, d) as crosslinkers/curing agents for resins, e) as primers in paints, f) as wet-adhesion promoters in emulsion paints, g) as complexing agents and flocculating agents, h) as penetration assistants in wood preservation, i) as corrosion inhibitors, j) as immobilizing agents for proteins and enzymes.

The invention is illustrated in more detail by the examples without the examples limiting the subject matter of the invention.

EXAMPLES

The average molecular weight of the oligomers was determined by gel permeation chromatography in accordance with the method of size exclusion chromatography. The eluent used was hexafluoroisopropanol with 0.05% of potassium trifluoroacetate. The measurement was carried out at 40° C. with a flow rate of 1 ml/min on a styrene-divinylbenzene copolymer column (8 mm*30 cm) with an RI differential refractometer or UV photometer as detector. Calibration took place using narrow-range PMMA standards.

For the measurement of the Hazen color number (in accordance with APHA), the sample is diluted 1:2500 with a diluent which does not absorb in the range from 380 to 720 nm. The Hazen color number is then determined in a range from 380 to 720 nm, in 10 nm steps.

Generally speaking, the color numbers of the polyethylenepolyamines which are prepared with the processes of the known prior art are more than 100, in some cases more than 200, and in certain cases even more than 600.

Example 1

A 250 ml autoclave with paddle stirrer was charged under inert conditions, for the exclusion of oxygen, with 12.1 g (7.63 mmol) of [Ru(Pnoctyl$_3$)$_4$(H)$_2$], 450 g (7.37 mol) of ethanolamine, 10.05 g (89.56 mmol) of potassium tert-butoxide and 1620 ml of toluene. In the closed autoclave, hydrogen was injected to 40 bar. Then the reaction mixture was heated to 140° C. and stirred for 20 hours. Following completed reaction and cooling, two phases were formed. The upper phase, which contains the catalyst, was separated from the lower phase, which contains the product. The product phase was extracted by shaking with toluene. Then the water of reaction, the unreacted reactant and volatile constituents were removed on a rotary evaporator at 12 mbar and 116° C., giving 115.66 g of the pure product. The weight average (RI) of the oligomer obtained was at 1470 g/mol, with a dispersity (Mw/Mn) of 2.8. This corresponds to an average chain length n for the oligomer (CH$_2$CH$_2$NH)$_n$ of 34. The color number was 20.

Example 2

A 250 ml autoclave with paddle stirrer was charged under inert conditions with 0.27 g (0.17 mmol) of [Ru(Pnoctyl$_3$)$_4$(H)$_2$], 10.5 g of the discharge from example 1, 230 mg (2.05 mmol) of potassium tert-butoxide and 37 ml of toluene. In the closed autoclave the reaction mixture is stirred at 140° C. under the intrinsic pressure of the solvent for 10 hours. Following completed reaction and cooling, the product has precipitated as a solid. The batch is quenched with 200 ml of water, with the product dissolving and forming two phases. The upper phase, which contains the catalyst, was separated from the lower phase, which contains the product. The water of reaction, the unreacted reactant and volatile constituents were removed on a rotary evaporator at 12 mbar and 116° C., giving 9.42 g of the pure product. The weight average (RI) of the oligomer obtained was at 1520 g/mol, with a dispersity (Mw/Mn) of 3.4. This corresponds to an average chain length n for the oligomer $(CH_2CH_2NH)_n$ of 35. The color number was 71.

Example 3

A 250 ml autoclave with paddle stirrer was charged under inert conditions with 0.27 g (0.17 mmol) of $[Ru(Pnoctyl_3)_4(H)_2]$, 10.5 g of the discharge from example 1, 230 mg (2.05 mmol) of potassium tert-butoxide and 37 ml of toluene. In the closed autoclave, hydrogen was injected to 15 bar. Subsequently the reaction mixture was heated to 140° C. and stirred for 10 hours. Following completed reaction and cooling, the product has precipitated as a solid. The batch is quenched with 200 ml of water, with the product dissolving and forming two phases. The upper phase, which contains the catalyst, was separated from the lower phase, which contains the product. The water of reaction, the unreacted reactant and volatile constituents were removed on a rotary evaporator at 12 mbar and 116° C., giving the pure product. The weight average (RI) of the oligomer obtained was at 1170 g/mol, with a dispersity (Mw/Mn) of 3.4. This corresponds to an average chain length n for the oligomer $(CH_2CH_2NH)_n$ of 27. The color number was 54.

Example 4

A 250 ml autoclave with paddle stirrer was charged under inert conditions with 0.20 g (0.71 mmol) of $[Ru(COD)Cl_2]$, 0.50 g (2.9 mmol) of 1-butyl-3-methylimidazolium chloride, 12.1 g (0.06 mol) of 1,2-dodecanediol, 20.0 g (0.27 mol) of 1,3-propylenediamine, 0.50 g (4.46 mmol) of potassium tert-butoxide and 34 ml of toluene. In the closed autoclave the reaction mixture was stirred at 150° C. under the intrinsic pressure of the solvent for 20 hours. Following completed reaction and cooling, 5 ml of water were added to the reaction mixture, which was shaken, to give a solution (50.0 g) of the product in toluene, and also an aqueous solution (12.66 g) of the catalyst. The phases were separated. From the product phase, the unreacted reactant and volatile constituents were removed on a rotary evaporator at 20 mbar and 120° C., giving 14.13 g of the pure product. The weight average (RI) of the oligomer obtained was at 1470 g/mol, with a dispersity (Mw/Mn) of 3.9. This corresponds to an average chain length n for the oligomer $(CH_2CH(C_{10}H_{21})NHCH_2CH_2NH)_n$ of 6. The color number was 74.

Example 5

A 250 ml autoclave with paddle stirrer was charged under inert conditions with 0.20 g (0.71 mmol) of $[Ru(COD)Cl_2]$, 0.50 g (2.9 mmol) of 1-butyl-3-methylimidazolium chloride, 12.1 g (0.06 mol) of 1,2-dodecanediol, 20.0 g (0.27 mol) of 1,3-propylenediamine, 0.50 g (4.46 mmol) of potassium tert-butoxide and 34 ml of toluene. In the closed autoclave, hydrogen is injected to 40 bar. Subsequently the reaction mixture is heated to 150° C. and stirred for 20 hours. Following completed reaction and cooling, 20 ml of water were added to the reaction mixture, which was shaken, to give a solution of the product in toluene, and also an aqueous solution of the catalyst. The phases were separated. From the product phase, the unreacted reactant and volatile constituents were removed on a rotary evaporator at 20 mbar and 120° C., giving 11.97 g of the pure product. The weight average (RI) of the oligomer obtained was at 1470 g/mol, with a dispersity (Mw/Mn) of 3.9. This corresponds to an average chain length n for the oligomer $(CH_2CH(C_{10}H_{21})NHCH_2CH_2NH)_n$ of 6. The color number was 21.

Comparative Example 1

An autoclave with paddle stirrer was charged under inert conditions with 10 g (0.36 mmol) of $[Ru(COD)(Cl)_2]_2$, 0.22 g of Triphos (0.36 mmol), 0.2 g of tri-n-octylphosphine (0.54 mmol), 10 g (0.16 mol) of ethanolamine, 0.15 g (1.3 mmol) of potassium tert-butoxide and 60 g of toluene. Subsequently the reaction mixture was heated to 140° C. and stirred for 20 hours. Following completed reaction and cooling, the batch was admixed with 10 ml of water. The upper phase was separated from the lower phase, which contained the product. Subsequently the water, unreacted reactants and volatile constituents were removed on a rotary evaporator at 12 mbar and 110° C., giving 6.5 g of the pure product. The color number was 871.

The invention claimed is:

1. A process for the preparation of polyalkylenepolyamines by homogeneously catalyzed alcohol amination, in which
   (i) aliphatic amino alcohols are reacted with one another or
   (ii) aliphatic diamines or polyamines are reacted with aliphatic diols or polyols with the elimination of water in the presence of a homogeneous catalyst and in the presence of hydrogen gas.

2. The process according to claim 1, wherein the reaction is carried out at a partial pressure of the hydrogen gas of from 0.1 to 25 MPa.

3. The process according to claim 1 or 2, wherein the catalyst is a transition metal complex catalyst.

4. The process according to claim 1, wherein the catalyst comprises ruthenium or iridium.

5. The process according to claim 1, wherein the catalyst comprises a nitrogen-heterocyclic carbene ligand.

6. The process according to claim 5, wherein the catalyst comprises a carbene ligand from the group consisting of 1-butyl-3-methylimidazolin-2-ylidene, 1-ethyl-3-methylimidazolin-2-ylidene, 1-methylimidazolin-2-ylidene, dipropylimidazolin-2-ylidene.

7. The process according to claim 1, wherein the catalyst comprises a monodentate or polydentate phosphine ligand.

8. The process according to claim 7, wherein the catalyst comprises a monodentate phosphine ligand comprising an unbranched, acyclic or cyclic aliphatic radical having from 1 to 12 carbon atoms or an aryliphatic radical.

9. The process according to claim 7, wherein the catalyst comprises a monodentate phosphine ligand, selected from the group consisting of triphenylphosphine, tritolylphosphine, tri-n-butylphosphine, tri-n-octylphosphine, trimethylphosphine, triethylphosphine, di(1-adamantyl)-n-butylphosphine, di(1-adamantyl)benzylphosphine, 2-(dicyclohexylphosphino)-1-phenyl-1H-pyrrole.

10. The process according to claim 7, wherein the catalyst comprises a polydentate phosphine ligand consisting of at least one unbranched, acyclic or cyclic aliphatic radical having 1 to 12 carbon atoms or aryliphatic radical.

11. The process according to claim 7, wherein the catalyst comprises a polydentate phosphine ligand selected from the group consisting of bis(diphenylphosphino)methane, 1,2-bis (diphenylphosphino)ethane, 1,2-dimethyl-1,2-bis(diphenylphosphino)ethane, 1,2-bis(dicyclohexylphosphino) ethane, 1,2-bis(diethylphosphino)ethane, 1,3-bis (diphenylphosphino)propane, 1,4-bis(diphenylphosphino) butane, 2,3-bis(diphenylphosphino)butane, 1,1,1-tris (diphenylphosphinomethyl)ethane, 1,1'-bis (diphenylphosphanyl)ferrocene and 4,5-bis (diphenylphosphino)-9,9-dimethylxanthene.

12. The process according to claim 1, wherein the catalyst comprises a ligand selected from the group consisting of cyclopentadienyl, substituted cyclopentadienyl, indenyl and substituted indenyl.

13. The process according to claim 1, wherein the catalyst comprises a ligand selected from the group consisting of hydroxide, hydride, carbonyl and chloride.

14. The process according to claim 1, wherein the reaction is carried out in the presence of a solvent.

15. The process according to claim 14, wherein the solvent is selected from the group consisting of benzene, toluene, xylenes, alkanes, acyclic and cyclic ethers, alcohols having more than three carbon atoms.

16. The process according to claim 14, wherein the solvent is selected from the group consisting of water, ionic liquids, sulfoxides, formamides, acetonitrile.

17. The process according to claim 1, wherein at least one of the reactants—aliphatic amino alcohols, aliphatic diamines or polyamines or aliphatic diols or polyols—comprises an alkyl or alkylene group having five or more carbon atoms.

18. The process according to claim 1, wherein at least (i) monoethanolamine or (ii) ethylene glycol is reacted with ethylenediamine.

19. The process according to claim 1, wherein 3-aminopropan-1-ol is reacted.

20. The process according to claim 1, wherein at least ethylenediamine or 1,2-propylenediamine or 1,3-propylenediamine and 1,2-decanediol or 1,2-dodecanediol is selected.

21. The process according to claim 1, wherein at least one of the reactants—aliphatic amino alcohols, aliphatic diamines or polyamines or aliphatic diols or polyols—comprises an alkyl or alkylene group having from 2 to 4 carbon atoms.

22. The process according to claim 1, wherein at least one of the reactants—aliphatic amino alcohols, aliphatic diamines or polyamines or aliphatic diols or polyols—comprises an alkyl or alkylene group having from 5 to 20 carbon atoms.

23. The process according to claim 1, wherein the heteroatoms O or N of one of the starting materials—aliphatic amino alcohols, aliphatic diamines or polyamines or aliphatic diols or polyols—are located in alpha and beta position on the chain of carbon atoms and thus on adjacent carbon atoms.

24. The process according to claim 1, wherein the heteroatoms O or N of one of the starting materials—aliphatic amino alcohols, aliphatic diamines or polyamines or aliphatic diols or polyols—are located in alpha and omega position on the chain of carbon atoms and thus at opposite ends of the chain of carbon atoms.

* * * * *